US010463747B2

(12) United States Patent
Celis

(10) Patent No.: US 10,463,747 B2
(45) Date of Patent: Nov. 5, 2019

(54) METHOD OF DEVELOPING A VACCINE USING PEPTIDE-POLY IC COMPLEXES

(71) Applicant: H. Lee Moffitt Cancer Center and Research Institute, Inc., Tampa, FL (US)

(72) Inventor: Esteban Celis, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 128 days.

(21) Appl. No.: 15/682,029

(22) Filed: Aug. 21, 2017

(65) Prior Publication Data

US 2018/0055945 A1 Mar. 1, 2018

Related U.S. Application Data

(60) Division of application No. 14/048,714, filed on Oct. 8, 2013, now Pat. No. 9,770,513, which is a continuation of application No. PCT/US2012/032708, filed on Apr. 9, 2012.

(60) Provisional application No. 61/602,668, filed on Feb. 24, 2012, provisional application No. 61/473,337, filed on Apr. 8, 2011.

(51) Int. Cl.

| | |
|---|---|
| ***A61K 39/395*** | (2006.01) |
| ***A61K 47/64*** | (2017.01) |
| ***A61K 47/61*** | (2017.01) |
| ***A61K 39/00*** | (2006.01) |
| ***A61K 39/12*** | (2006.01) |
| ***A61K 47/54*** | (2017.01) |
| ***A61K 47/55*** | (2017.01) |

(52) U.S. Cl.

CPC ........ *A61K 47/646* (2017.08); *A61K 39/0011* (2013.01); *A61K 39/12* (2013.01); *A61K 47/549* (2017.08); *A61K 47/55* (2017.08); *A61K 47/61* (2017.08); *A61K 47/645* (2017.08); *A61K 47/6455* (2017.08); *A61K 2039/55561* (2013.01); *A61K 2039/57* (2013.01); *A61K 2039/627* (2013.01)

(58) Field of Classification Search

None

See application file for complete search history.

(56) References Cited

U.S. PATENT DOCUMENTS

2006/0222656 A1* 10/2006 Strome .............. A61K 39/0011 424/185.1

2009/0155308 A1 6/2009 Moon et al.

* cited by examiner

*Primary Examiner* — Yunsoo Kim

(74) *Attorney, Agent, or Firm* — Michele L. Lawson; Smith & Hopen, P.A.

(57) ABSTRACT

The invention describes the development of more potent peptide vaccines to prevent or treat infections or cancer and their administration to a subject in order to elicit a T cell response in the subject. Small synthetic peptides from the known sequences of viral, bacterial, parasitic or tumor antigens are modified so they can spontaneously form complexes with a synthetic nucleic acid, such as Poly IC, that functions as an immunological adjuvant. The peptide-nucleic acid complexes are dramatically more immunogenic as compared to the separate components. The procedure for developing the vaccine involves the conjugation of a synthetic peptide containing a C residue to poly-K using a bi-functional cross-linking reagent (SMCC). The peptide/poly-K complex was then formulated with CMC and poly-IC to produce a self-adjuvant vaccine that was 36-fold more effective as compared to the same peptide administered mixed with the same adjuvant (but not complexed to it).

13 Claims, 11 Drawing Sheets

Specification includes a Sequence Listing.

(R)$_7$-MFV-TAPDNLGYM (K)$_7$-MFV-TAPDNLGYM (E)$_7$-MFV-TAPDNLGYM

CD8$^+$ 23.3 29.9 31.3

Trp1$_{455-463}$ Tetramer

CD8$^+$ 1.23 1.35 1.59

Trp1$_{455-463}$ Tetramer

CD8$^+$ 2.87 4.89 5.12

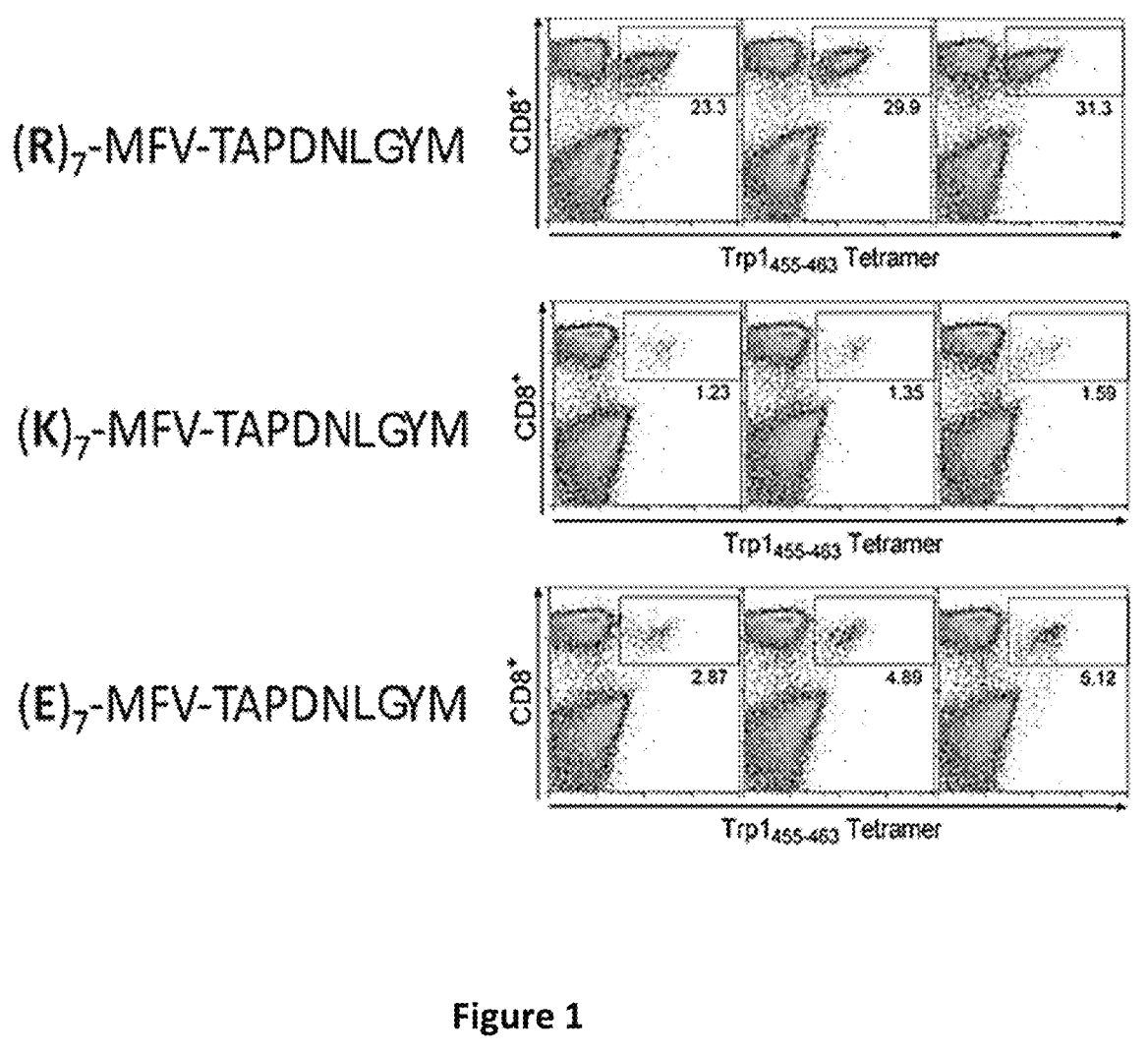

Trp1$_{455-463}$ Tetramer

Figure 1

(R3)MFVTAPDNLGYM (R7)MFVTAPDNLGYM

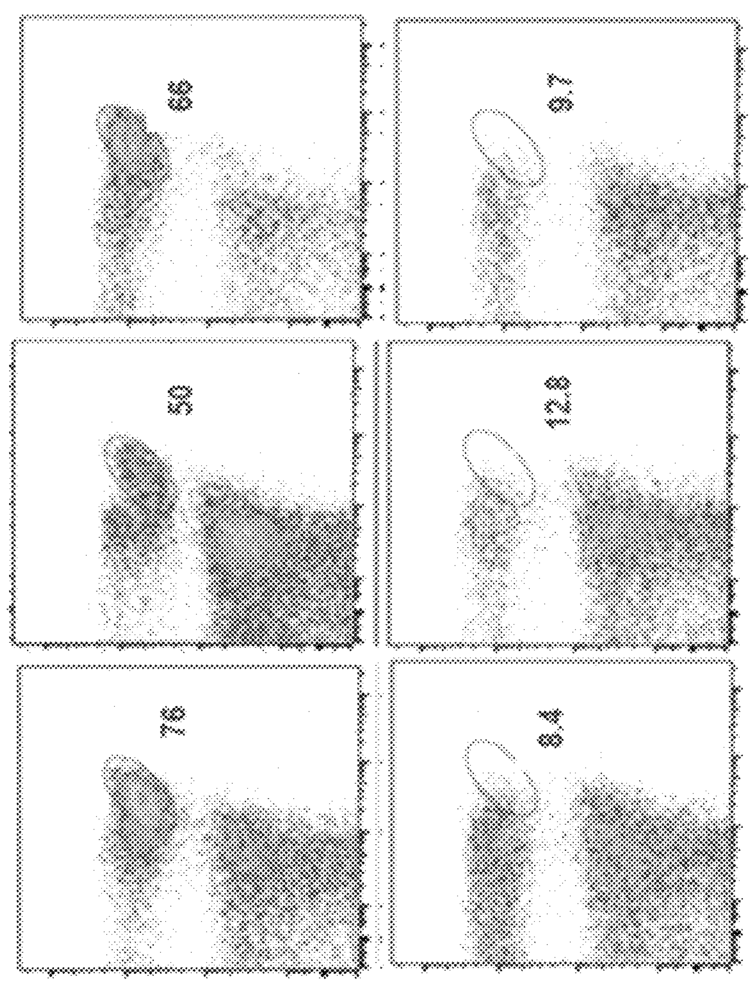
Figure 8
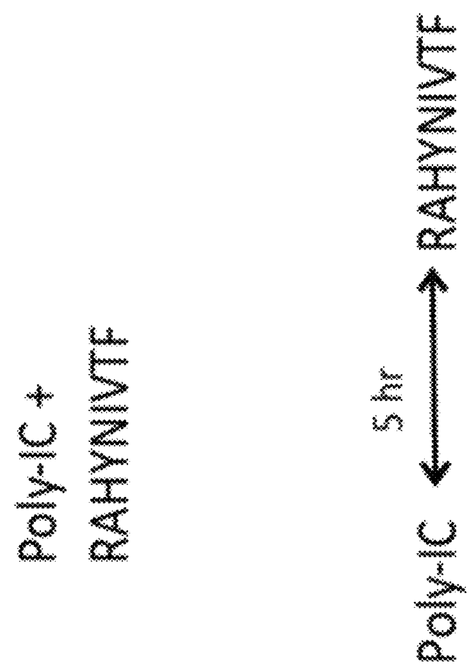

SEQUENCE LISTING

<160> NUMBER OF SEQ ID NOS: 15

<210> SEQ ID NO 1
<211> LENGTH: 6
<212> TYPE: PRT
<213> ORGANISM: artificial sequence
<220> FEATURE:
<223> OTHER INFORMATION: hydrophic residue string to add to epitope

<400> SEQUENCE: 1

Met Phe Val Met Phe Val
1 5

<210> SEQ ID NO 2
<211> LENGTH: 9
<212> TYPE: PRT
<213> ORGANISM: artificial sequence
<220> FEATURE:
<223> OTHER INFORMATION: peptide epitope Trp 1 455/9m

<400> SEQUENCE: 2

Thr Ala Pro Asp Asn Leu Gly Tyr Met
1 5

<210> SEQ ID NO 3
<211> LENGTH: 3
<212> TYPE: PRT
<213> ORGANISM: artificial sequence
<220> FEATURE:
<223> OTHER INFORMATION: 3 amino acid linking sequence

<400> SEQUENCE: 3

Met Phe Val
1

<210> SEQ ID NO 4
<211> LENGTH: 19
<212> TYPE: PRT
<213> ORGANISM: artificial sequence
<220> FEATURE:
<223> OTHER INFORMATION: 7 arginine tail epitope Trp1 455/9m

<400> SEQUENCE: 4

Arg Arg Arg Arg Arg Arg Arg Met Phe Val Thr Ala Pro Asp Asn Leu
1 5 10 15

Gly Tyr Met

<210> SEQ ID NO 5
<211> LENGTH: 19
<212> TYPE: PRT
<213> ORGANISM: artificial sequence
<220> FEATURE:
<223> OTHER INFORMATION: 7 lysine tail epitope Trp1 455/9m

<400> SEQUENCE: 5

Lys Lys Lys Lys Lys Lys Lys Met Phe Val Thr Ala Pro Asp Asn Leu 1 5 10 15

Gly Tyr Met

<210> SEQ ID NO 6
<211> LENGTH: 19
<212> TYPE: PRT
<213> ORGANISM: artificial sequence
<220> FEATURE:
<223> OTHER INFORMATION: 7 glutamic acid tail epitope Trp1 455/9m

<400> SEQUENCE: 6

Glu Glu Glu Glu Glu Glu Glu Met Phe Val Thr Ala Pro Asp Asn Leu
1 5 10 15

Gly Tyr Met

<210> SEQ ID NO 7
<211> LENGTH: 15
<212> TYPE: PRT
<213> ORGANISM: artificial sequence
<220> FEATURE:
<223> OTHER INFORMATION: 3 arginine tail epitope Trp1 455/9m

<400> SEQUENCE: 7

Arg Arg Arg Met Phe Val Thr Ala Pro Asp Asn Leu Gly Tyr Met
1 5 10 15

<210> SEQ ID NO 8
<211> LENGTH: 9
<212> TYPE: PRT
<213> ORGANISM: artificial sequence
<220> FEATURE:
<223> OTHER INFORMATION: peptide epitope hpv16-e7 49

<400> SEQUENCE: 8

Arg Ala His Tyr Asn Ile Val Thr Phe
1 5

<210> SEQ ID NO 9
<211> LENGTH: 9
<212> TYPE: PRT
<213> ORGANISM: artificial sequence
<220> FEATURE:
<223> OTHER INFORMATION: peptide epitope hpv16-e7 49/1a

<400> SEQUENCE: 9

Ala Ala His Tyr Asn Ile Val Thr Phe
1 5

<210> SEQ ID NO 10
<211> LENGTH: 16
<212> TYPE: PRT
<213> ORGANISM: artificial sequence
<220> FEATURE:
<223> OTHER INFORMATION: peptide epitope Trp1 455/9m with hydrophobic tail

<400> SEQUENCE: 10

Leu Met Phe Val Met Phe Val Thr Ala Pro Asp Asn Leu Gly Tyr Met
1 5 10 15

<210> SEQ ID NO 11
<211> LENGTH: 13
<212> TYPE: PRT
<213> ORGANISM: artificial sequence
<220> FEATURE:
<223> OTHER INFORMATION: Trp1 455/9m with hydrophobic tail (Pam)2 KMFV

```
<400> SEQUENCE: 11

Lys Met Phe Val Thr Ala Pro Asp Asn Leu Gly Tyr Met
1               5                   10


<210> SEQ ID NO 12
<211> LENGTH: 6
<212> TYPE: PRT
<213> ORGANISM: artificial sequence
<220> FEATURE:
<223> OTHER INFORMATION: 6 hydrophobic amino acid chain LMFMFV

<400> SEQUENCE: 12

Leu Met Phe Met Phe Val
1               5


<210> SEQ ID NO 13
<211> LENGTH: 8
<212> TYPE: PRT
<213> ORGANISM: artificial sequence
<220> FEATURE:
<223> OTHER INFORMATION: 8 hydrophobic amino acid epitope

<400> SEQUENCE: 13

Ser Val Asp Phe Phe Val Trp Leu
1               5


<210> SEQ ID NO 14
<211> LENGTH: 2
<212> TYPE: PRT
<213> ORGANISM: artificial sequence
<220> FEATURE:
<223> OTHER INFORMATION: hydrophilic amino acid linker

<400> SEQUENCE: 14

Ser Ser
1


<210> SEQ ID NO 15
<211> LENGTH: 12
<212> TYPE: PRT
<213> ORGANISM: artificial sequence
<220> FEATURE:
<223> OTHER INFORMATION: peptide with hydrophilic linker and minimal T
      cell epitope

<400> SEQUENCE: 15

Cys Ser Ser Thr Ala Pro Asp Asn Leu Gly Tyr Met
1               5                   10
```

METHOD OF DEVELOPING A VACCINE USING PEPTIDE-POLY IC COMPLEXES

CROSS REFERENCE TO RELATED APPLICATIONS

This application is a divisional of and claims priority to currently pending U.S. application Ser. No. 14/048,714 entitled "Method of Developing a Vaccine Using Peptide-Poly IC Complexes", filed Oct. 8, 2013, which is a continuation of prior filed International Application, Serial Number PCT/US2012/032708, filed on Apr. 9, 2012, which claims priority to U.S. Provisional Application No. 61/602,668 entitled "Method of Developing a Vaccine Using Peptide-Poly IC Complexes", filed Feb. 24, 2012, and U.S. Provisional Application No. 61/473,337 entitled "Method of Developing a Vaccine Using Peptide-Poly IC Complexes", filed Apr. 8, 2011, the contents of each of which are hereby incorporated by reference into this disclosure.

GOVERNMENTAL SUPPORT

This invention was made with Government support under Grant No. R01CA136828 awarded by the National Institutes of Health (NIH). The Government has certain rights in the invention.

FIELD OF INVENTION

This invention relates to vaccines. Specifically, the invention provides methods of modifying peptide antigens to enhance their immunogenicity by facilitating the formation of complexes with an immune adjuvant.

BACKGROUND OF THE INVENTION

A vaccine may contain a wide variety of different antigens ranging from whole-killed organisms such as inactivated viruses or bacteria, fungi, protozoa, or cancer cells to sub-fractions of these organisms/tissues, proteins or peptides. Antigens can be recognized by the immune system in the form of proteins or peptides and can contain polysaccharides and/or lipids. Short peptides can be used since cytotoxic T cells recognize antigens in the form of short, usually about 8-16 amino acids long, peptides in conjunction with major histocompatibility complex (MHC).

Peptides are increasingly important in vaccine design. It has been shown that co-injection of a mixture of poly-L-arginine or poly-L-lysine together with an appropriate peptide as a vaccine protects animals from tumor growth in mouse models. (Buschle et al., Gene Ther Mol Biol (1998) 1:309-321 and Schmidt et al., PNAS (1997) 94:3262-3267). This vaccine is able to induce high numbers of antigen/peptide-specific T cells.

In order to induce antigen-specific T cells, peptides must be taken up by antigen presenting cells (APCs). APCs induce an immune cascade which eventually leads to the induction of antigen-specific immune effector cells such as cytotoxic T cells. However, it is a well-recognized problem in the art that many peptides defining antigenic regions of medically important pathogens fail to provide a sufficient immune response in vivo.

Essentially, any peptide that is able to bind an MHC molecule may function as a T cell epitope. The presence of a T cell with a corresponding T cell receptor (TCR) and the absence of tolerance for this particular epitope are prerequisites for the induction of an in vitro or in vivo T cell response. T helper cells orchestrate the effector function of CTLs in anti-tumor immunity. T helper cell epitopes that trigger a T helper cell response of the TH1 type support effector functions of CD8+ killer T cells, which include cytotoxic functions directed against tumor cells displaying tumor-associated peptide/MHC complexes on the cell surface. In this way, tumor-associated T helper cell peptide epitopes, alone or in combination with other tumor-associated peptides can serve as pharmaceutical ingredients of vaccine compositions that stimulate anti-tumor immune responses.

Adjuvants must trigger immune cascades that involve all cells of the immune system that are necessary in order to obtain a sustained, antigen-specific immune response. Adjuvants primarily act on antigen presenting cells (APCs) such as dendritic cells (DC). These cells are normally the first cells to encounter an antigen followed by presentation of processed or unmodified antigen to immune effector cells. While intermediate cell types may be involved, only effector cells with the appropriate specificity are activated in a protective immune response. Adjuvants may locally retain antigens and co-injected other factors as well as act as chemoattractants for other immune cells. Adjuvants may also act locally and/or systemically as a stimulating agent for the immune system.

Polyinosinic-polycytidylic acid (poly IC) is a potent interferon I inducer. Poly-IC is a synthetic double stranded nucleic acid that functions as an immune adjuvant, stimulating pattern recognition receptors (PRRs), such as the toll-like receptor-3 (TLR3) and cytoplasmic helicases (RIG-I-like receptors) that are present on specialized antigen-presenting cells such as dendritic cells (DCs). In addition, Poly-IC is able to target the associated peptide antigen to DCs via scavenger receptors (SRs). Due to its protective effects in a number of different animal species against a broad spectrum of both RNA and DNA viruses, poly IC is often used in models of viral infections. The changes that occur in response to poly IC are thought to be representative of changes that occur in response to a variety of different viruses. Poly IC is known to stimulate macrophages to produce cytokines such as IL-1a and IL-12. It is also known as a potent NK cell stimulator and promotes Th-1 specific immune responses. Poly IC also induces stable maturation of in vitro cultured dendritic cells and that such dendritic cells are potent T cell stimulators in vitro. Due to these attributes, poly IC has been widely used as an immunomodulator in several clinical studies.

The prior art has failed to adequately address the problem of developing an effective vaccine which allows effective delivery of a specific antigen to the immune system in order to activate antigen-specific T cells against that specific antigen in a subject.

SUMMARY OF INVENTION

Synthetic peptides corresponding to known CD8 and CD4 T cell epitopes for infectious agents or tumor antigens can be modified to enable them to associate non-covalently with synthetic nucleic acids that function as immune adjuvants to form potent vaccines.

The inventors have observed that peptides representing T cell epitopes that are modified by the addition of either the cationic amino acids arginine (R), lysine (K), a small stretch of hydrophobic residues (e.g., MFVMFV) (SEQ ID NO:1) or lipids (e.g., palmitic acids) become highly immunogenic, generating large numbers of antigen-specific CD8 T lymphocytes when administered together as a mix with the immune adjuvant, polyinosinic:polycytidylic acid (Poly-IC). The modified peptides can associate via ionic bonds and/or hydrophobic interactions with Poly-IC.

The results indicated that immunogenicity of modified peptide-Poly-IC complexes is far superior as compared to unmodified peptides that are mixed with Poly-IC which cannot form complexes. These complexes can be used as prophylactic or therapeutic vaccines against various types of infectious diseases (viral, bacterial, protozoan, parasitic) or malignant disorders.

BRIEF DESCRIPTION OF THE DRAWINGS

For a fuller understanding of the invention, reference should be made to the following detailed description, taken in connection with the accompanying drawings, in which:

FIG. 1 is an image depicting a hepta-arginine $(R)_7$ tail increases the immunogenicity of a peptide epitope. CD8 T cell responses of peptide epitope $Trp1_{455/9}M$ (TAPDNLGYM) (SEQ ID NO:2) containing 3 types of tails with charged amino acids (R, K or E) and a short linker (MFV) (SEQ ID NO:3) were measured by tetramer analysis after i.v. prime-boost (2 weeks apart) vaccination using 120 μg peptide mixed with 50 μg Poly-IC. These sequences correspond to $(R)_7$-MFV-TAPDNLGYM (SEQ ID NO:4); $(K)_7$-MFV-TAPDNLGYM (SEQ ID NO:5); and $(E)_7$-MFV-TAPDNLGYM (SEQ ID NO:6) respectively. Immune responses in 3 individual mice measured 7 days after the boost in blood samples. Numbers below the rectangular gates correspond to the % tetramer positive (antigen-specific) cells of the total CD8 T cell population.

FIG. 8 is an image depicting that simultaneous administration of peptide and Poly-IC generates stronger immune responses as compared to injections 5 hours apart. Comparison of CD8 T cell responses of peptide epitope HPV16-$E7_{49}$ (RAHYNIVTF) (SEQ ID NO:8) injected together with 50 μg Poly-IC (top panels) or 5 hours after the Poly-IC (bottom panels). Immune responses in 3 individual mice measured 7 days after an identical boost (12 days apart) in blood samples. Numbers below the oval gates correspond to the % tetramer positive (antigen-specific) cells of the total CD8 T cell population.

DETAILED DESCRIPTION OF THE PREFERRED EMBODIMENT

Figure 2:
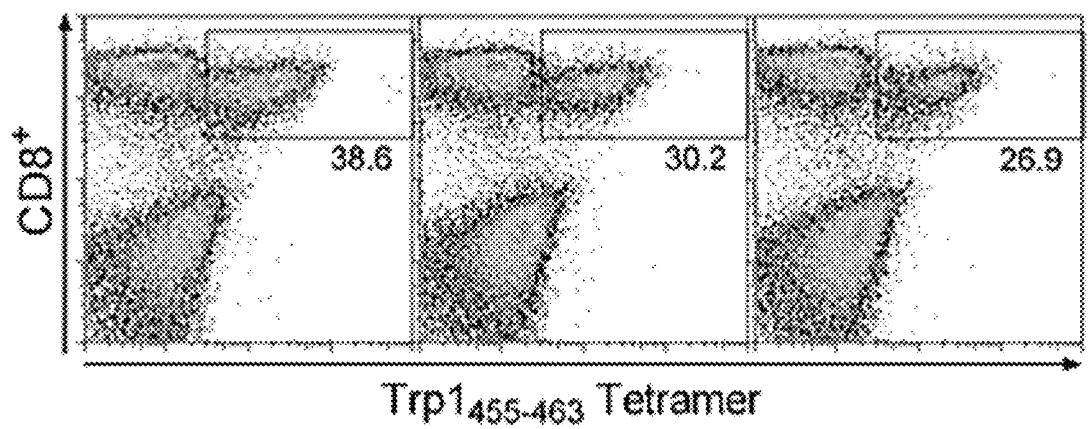
FIG. 2 is an image depicting a three-arginine $(R)_3$ tail increases immunogenicity of a peptide epitope similar to the results obtained from a hepta-arginine $(R)_7$ tail. The sequence for the three-arginine tail is $(R)_3$-MFVTAPDNLGYM (SEQ ID NO:7).
Figure 2:
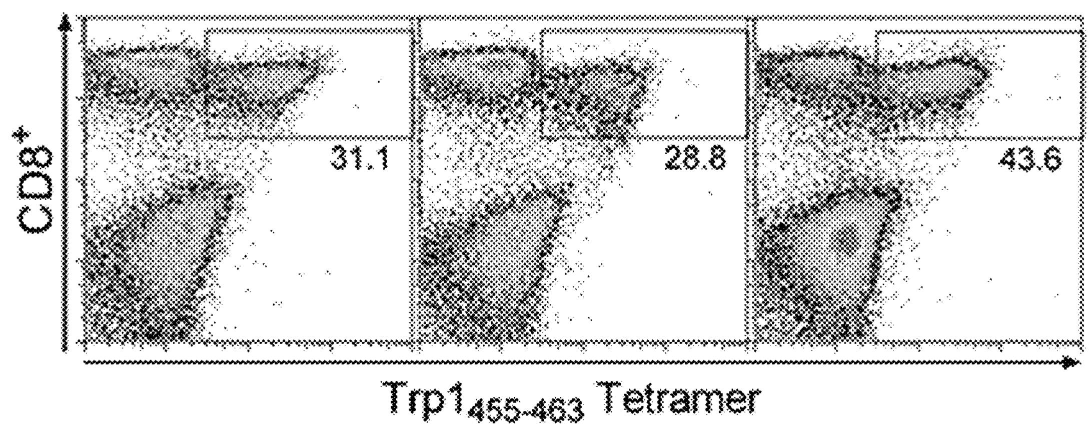

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed in the invention. The upper and lower limits of these smaller ranges may independently be excluded or included within the range. Each range where either, neither, or both limits are included in the smaller ranges are also encompassed by the invention, subject to any specifically excluded limit in the stated range. Where the stated range includes one or both of the limits, ranges excluding either or both of those excluded limits are also included in the invention.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

"Patient" is used to describe a vertebrate animal, preferably a human, to whom treatment is administered, including prophylactic treatment with the compositions of the present invention. The terms "patient" and "subject" are used interchangeably herein. Vertebrate animals include mammals such as humans, primates, canines, felines, bovines, porcines, equines, ayes, ruminants, etc.

The term "adjuvant" as used herein refers to an agent that nonspecifically increases an immune response to a particular antigen thereby reducing the quantity of antigen necessary in any given vaccine and/or the frequency of injection necessary in order to generate an adequate immune response to the antigen of interest. Suitable adjuvants for use herein include, but are not limited to, poly IC; synthetic oligodeoxynucleotides (ODNs) with a CpG motif; modified polyinosinic: polycytidylic acid (Poly-IC) including, but not limited to, Poly-IC/LC (Hiltonol) and Poly-IC12U (Ampligen); Poly-K; carboxymethyl cellulose (CMC); Adjuvant 65 (containing peanut oil, mannide monooleate, an aluminum monostearate); Freund's complete or incomplete adjuvant; mineral gels such as aluminum hydroxide, aluminum phosphate, and alum; surfactants such as hexadecylamine, octadecylamine, lysolecithin, dimethyldioctadecylammonium bromide, N,N-dioctadecyl-N',N"-bis(2-hydroxymethyl)propanediamine, methoxyhexadecylglyerol and pluronic polyols; polyanions such as pyran, dextran sulfate, polyacrylic acid, and carbopol; peptides such as muramyl dipeptide, dimethylglycine and tuftsin; and oil emulsions. The adjuvants of the present invention may include nucleic acids based on inosine and cytosine such as poly I:poly C; poly IC; poly dC; poly dI; poly dIC; Poly-IC/LC; Poly-K; and Poly-IC12U as well as oligodeoxynucleotides (ODNs) with a CpG motif, CMC and any other combinations of complementary double stranded IC sequences or chemically modified nucleic acids such as thiolated poly IC as described in U.S. Pat. Nos. 6,008,334; 3,679,654 and 3,725,545.

The term "peptide" as used herein refers to a series of amino acid residues that are connected to one another typically by peptide bonds between the alpha-amino and carbonyl groups of the adjacent amino acids. The peptides may be between about 8 and about 15 amino acids in length.

The term "oligopeptide" as used herein refers to a series of amino acid residues that are connected to one another typically by peptide bonds between the alpha-amino and carbonyl groups of the adjacent amino acids. An oligopeptide is typically less than about 30 amino acid residues in length and more than about 16 amino acid residues in length.

The term "polypeptide" as used herein refers to a series of amino acid residues that are connected to one another typically by peptide bonds between the alpha-amino and carbonyl groups of the adjacent amino acids. A polypeptide is meant to refer to molecules containing more than about 30 amino acid residues.

The term "immunogen" as used herein refers to a molecule that is capable of inducing an immune response. In the case of the present invention, the molecule should be capable of inducing a T-cell response. A peptide, oligopeptide, or polypeptide of the present invention may be immunogenic, and thus an immunogen, if it is capable of inducing an immune response. The terms "immunogen" and "antigen" are used interchangeably herein.

The term "epitope" as used herein refers to a portion of a polypeptide or peptide that is recognized (i.e. specifically bound) by a B cell and/or a T cell surface antigen receptor. Epitopes may be generally identified using well known techniques by those of ordinary skill in the art. The term "T-cell epitope" as used herein refers to a short peptide that is bound to a class I or II MHC receptor thus forming a ternary complex that can be recognized by a T-cell bearing a matching T-cell receptor binding to the MHC/peptide complex with appropriate affinity. Peptides binding to MHC class I molecules are typically about 8-14 amino acids in length. T-cell epitopes that bind to MHC class II molecules are typically about 12-30 amino acids in length. In the case of peptides that bind to MHC class II molecules, the same peptide and corresponding T cell epitope may share a common core segment, but differ in the overall length due to flanking sequences of differing lengths upstream of the amino-terminus of the core sequence and downstream of its carboxy terminus, respectively. A T-cell epitope may be classified as an antigen if it elicits an immune response.

The term "DNA sequence" as used herein refers to both single stranded and double stranded DNA. The specific sequence, unless the context indicates otherwise, refers to the single strand DNA of such sequence, the duplex of such sequence with its complement (double stranded DNA) and the complement of such sequence.

The term "coding region" as used herein refers to that portion of a gene which either naturally or normally codes for the expression product of that gene in its natural genomic environment, i.e. the region coding in vivo for the native expression product of the gene. The coding region can be from a normal, mutated, or altered gene or a DNA sequence or gene wholly synthesized in the laboratory using methods well known to those of ordinary skill in the art.

The term "nucleotide sequence" as used herein refers to a heteropolymer of deoxyribonucleotides. The nucleotide sequence coding for a particular peptide, oligopeptide, or polypeptide may be naturally occurring or synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from microbial or viral operon.

The term "expression product" as used herein refers to the polypeptide or protein that is the natural translation product of the gene and any nucleic acid sequence coding equivalents resulting from genetic code degeneracy and thus coding for the same amino acid(s).

The term "T cell response" as used herein refers to the specific proliferation and activation of effector functions induced by a peptide in vitro or in vivo. For MHC class I restricted CTLs, effector functions may include, but are not limited to, lysis of peptide-pulsed, peptide-precursor pulsed, or naturally peptide-presenting target cells; secretion of cytokines, such as IFN-γ, TNF-α or IL-2 induced by a peptide; and secretion of effector molecules such as granzymes or perforins induced by peptide or degranulation. For MHC class II-restricted T helper cells, effector functions may include, but are not limited to, peptide induced secretion of cytokines such as IFN-γ, TNF-α, IL-4, IL-5, IL-10 or IL-2; or peptide induced degranulation.

The term "vaccine" as used herein refers to an antigenic composition usually comprising an infectious factor or a portion of an infectious factor, such as an antigen, in combination with an immune adjuvant, administered into the body to elicit an immune response. The antigenic portion may be a microorganism such as a virus or bacterium; a natural product purified from a microorganism; or a synthetic or genetically engineered protein, peptide, polysaccharide, or similar product. In a preferred embodiment, the antigenic portion of the vaccine of the present invention is comprised of a T cell epitope.

The vaccine compositions of the present invention may be formulated according to known methods, e.g. as intravenous (i.v.) vaccines, DNA vaccines, oral vaccines, transdermal vaccines, topical vaccines, intranasal vaccines, and as combination vaccines. The dosages may be selected by standard processes as known by those of ordinary skill in the art. For vaccines which are improvements on known vaccines, a lower dosage than the known vaccine dosage is possible for the same protection and is therefore preferred. The vaccine is may be provided in a storage stable form such as being lyophilized, optionally being provided in combination with a suitable reconstitution solution.

The "therapeutically effective amount" for purposes herein is thus determined by such considerations as are known in the art. A therapeutically effective amount of the vaccine described herein is that amount necessary to provide a therapeutically effective result in vivo or in vitro. The amount of vaccine administered must be effective to achieve a response, including but not limited to total prevention of (e.g., protection against) and to improved survival rate or more rapid recovery, or improvement or elimination of symptoms associated with the disorder or disease or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

"Administration" or "administering" is used to describe the process in which vaccine compositions of the present invention are delivered to a patient. The composition may be administered in various ways including parenteral (referring to intravenous and intraarterial and other appropriate parenteral routes), transdermal, intranasal, topical, among others.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, $19^{th}$ ed.) describes formulations which can be used in connection with the subject invention. "Pharmaceutical composition" and "vaccine" are used interchangeably herein.

The peptide-based vaccines disclosed herein are capable of being used in combination with another therapeutic. Examples of therapeutics that can be used in conjunction with the vaccines disclosed herein include, but are not limited to: immunomodulatory cytokines, including but not limited to, IL-2, IL-15, IL-7, IL-21, GM-CSF as well as any other cytokines that are capable of further enhancing immune responses; immunomodulatory antibodies, including but not limited to, anti-CTLA4, anti-CD40, anti-41BB, anti-OX40, anti-PD1 and anti-PDL1; and immunomodulatory drugs including, but not limited to, lenalidomide (Revlimid).

In addition, the peptide-based vaccines disclosed herein may be administered for cancer treatment in combination with chemotherapy in regimens that do not inhibit the immune system including, but not limited to, low dose cyclophosphamide and taxol. The vaccines may also be administered for cancer in combination with therapeutic antibodies including, but not limited to, anti-HER2/neu (Herceptin) and anti-CD20 (Rituxan).

The peptide-based vaccines can be administered for treatment of chronic infections in combination with drugs used to treat the particular type of infection including, but not limited to, anti-viral drugs, anti-retroviral drugs, anti-malarial drugs, etc.

Modification of Synthetic Peptides

Synthetic peptides corresponding to known CD8 and CD4 T cell epitopes for infectious agents or tumor antigens can be modified to enable them to associate either non-covalently or covalently with synthetic nucleic acids that function as immune adjuvants to form potent vaccines.

The inventors have observed that peptides representing T cell epitopes that are modified by the addition of either the cationic amino acid arginine (R), small stretch of hydrophobic residues (e.g., MFVMFV) (SEQ ID NO: 1), lipids (e.g., palmitic acids), or a combination of cationic amino acids and hydrophobic residues, become highly immunogenic, generating large numbers of antigen-specific CD8 T lymphocytes when administered together as a mix with an immune adjuvant, such has polyinosinic:polycytidylic acid (Poly-IC) or modified versions of Poly-IC. The modified peptides can associate via ionic bonds and/or hydrophobic interactions with immune adjuvants such as Poly-IC or modified versions of Poly-IC.

The epitopes used are normally between about 8-15 amino acids long and correspond to known CD8 and CD4 T cell epitopes for infectious agents or tumor antigens. Preferably, the epitopes can be between about 8 and about 11 amino acids long. The peptide itself may be up to about 40 amino acids long. Modifications may be made either within the epitope or at either end of the epitope to assist the epitope in interacting with Poly-IC. The locations of the modifications of the epitope depend on the specific epitope used.

Example 1—Addition of Cationic Amino Acid Tails

The results show that peptides containing an amino tail of seven arginines ($R_7$) function as good immunogens, while peptides containing tails of seven lysines ($K_7$) or seven glutamic acids ($E_7$) do not (FIG. 1). The results also show that fewer than seven arginines $(R)_7$ also function as good immunogens. For example, peptides of 3 arginines $(R)_3$ function as well as peptides with seven arginines $(R)_7$. (FIG. 2) Preferably, the number of arginines added to the peptide is between about 1 and about 10. The arginines are preferably added to the amino terminus but may also be added to the carboxy terminus.

Figure 3:
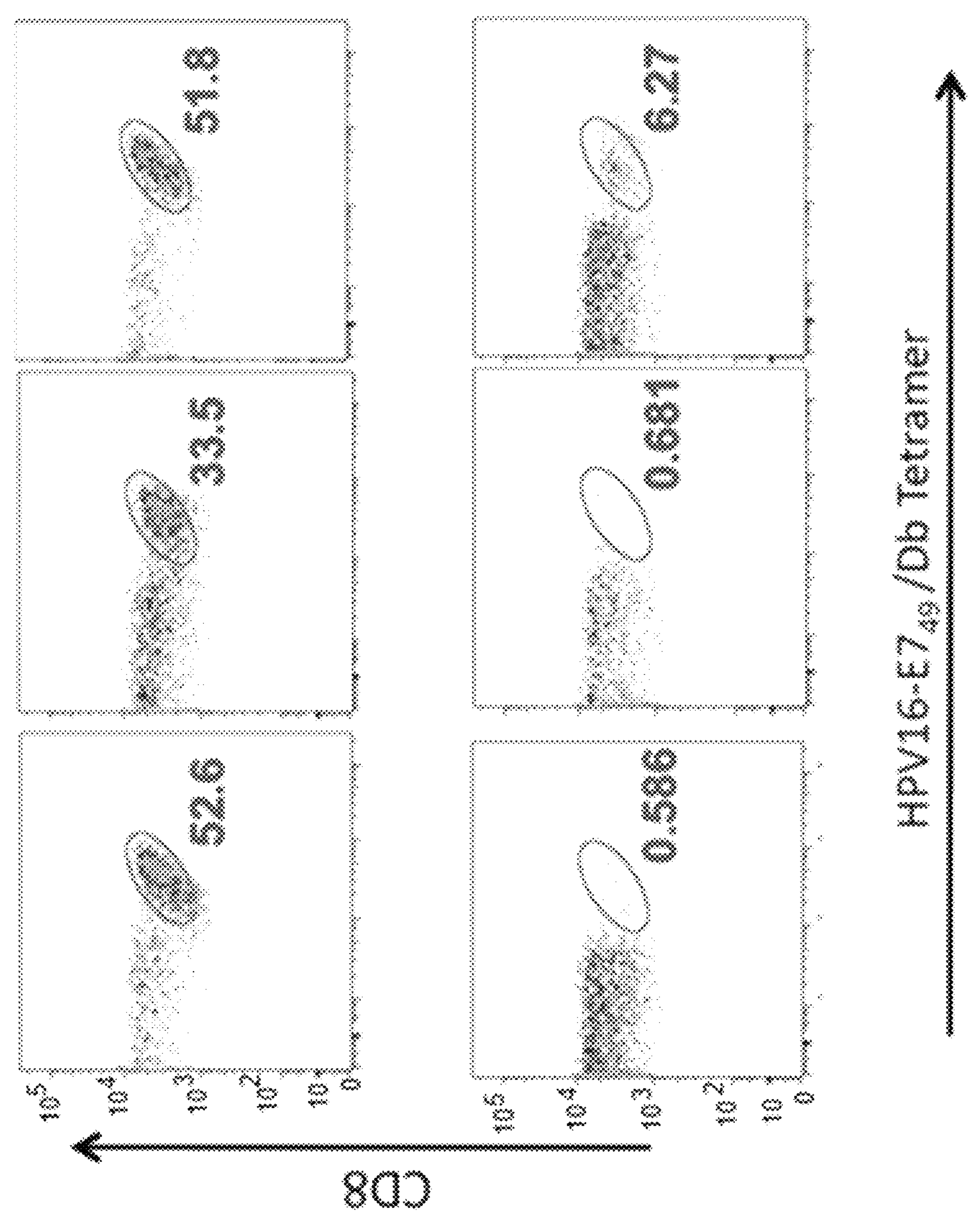
FIG. 3 is an image depicting alanine (A) substitution at position 1 in a peptide epitope naturally containing an arginine (R) reduces its immunogenicity. CD8 T cell responses of peptide epitope HPV16-$E7_{49}$ (RAHYNIVTF) (SEQ ID NO:8) and HPV16-$E7_{49/1A}$ (AAHYNIVTF) (SEQ ID NO:9) measured by tetramer analysis after i.v. prime-boost (2 weeks apart) vaccination using 30 μg peptide mixed with 50 μg Poly-IC. Immune responses in 3 individual mice measured 7 days after the boost in blood samples. Numbers below the oval gates correspond to the % tetramer positive (antigen-specific) cells of the total CD8 T cell population.

The inventors have observed a peptide epitope from human papilloma virus 16-E7 (HPV16-E7) that naturally has an arginine residue at position 1 (RAHYNIVTF) (SEQ ID NO: 8), that substitution of this arginine for an alanine (AAHYNIVTF) (SEQ ID NO:9) reduced dramatically the immunogenicity when administered with Poly-IC (FIG. 3). It has been reported that the substitution of arginine at position 1 of this epitope for an alanine does not interfere with the capacity of the peptide to bind to the MHC molecule and be recognized by T cells (Melero, I., et al., J. Virol. 71: 3998-4004; 1997). Thus, the inventors believe that RAHYNIVTF (SEQ ID NO: 8) is more immunogenic than AAHYNIVTF (SEQ ID NO: 9) because of the presence of the arginine at position 1 that allows the peptide to complex with Poly-IC.

Figure 4:
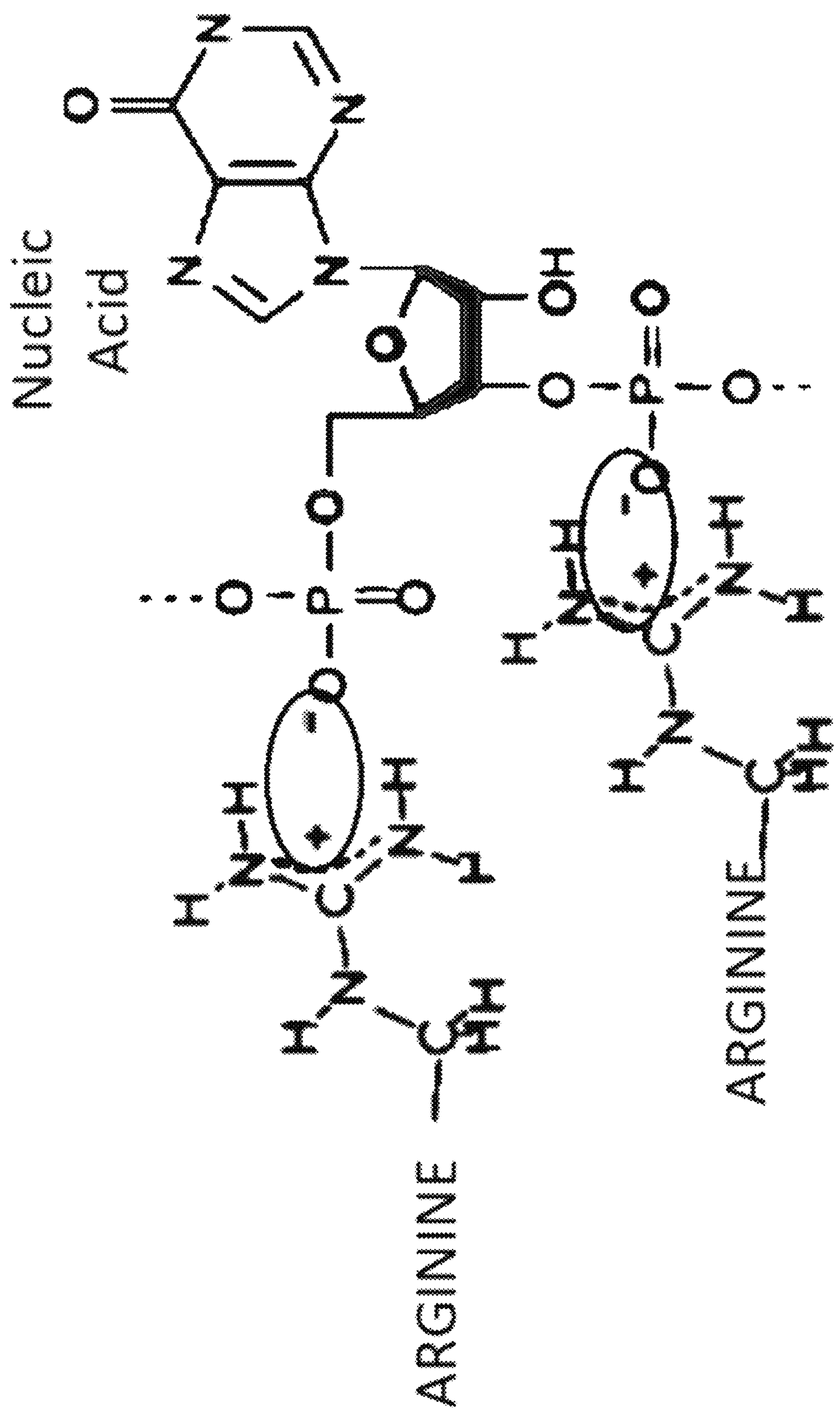
FIG. 4 is an image depicting the electrostatic (salt bridges) interactions between the positive charge of arginine and the negative phosphate group of Poly-IC may allow the formation of highly immunogenic molecular complexes.
Figure 5:
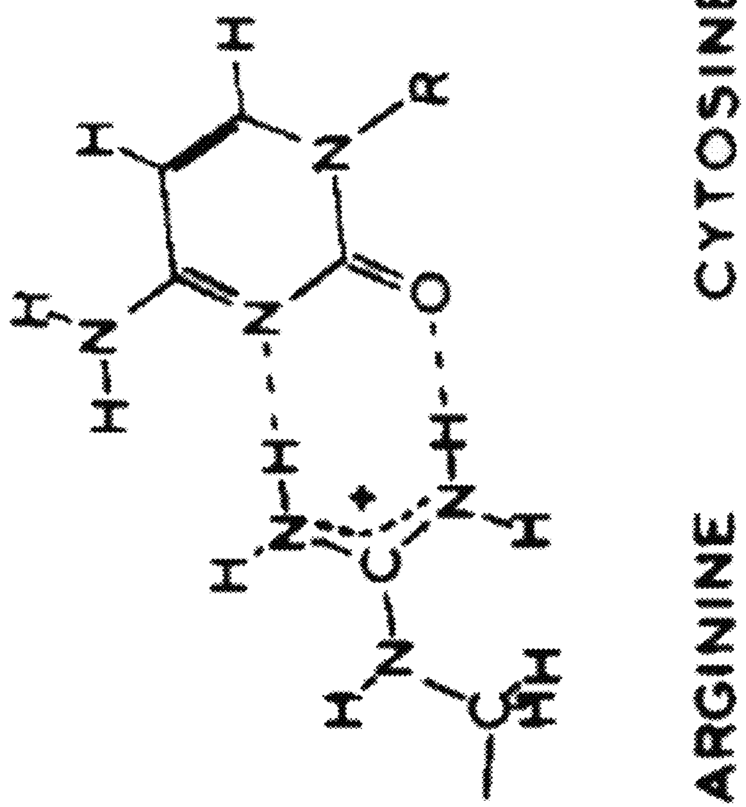
FIG. 5 is an image depicting the hydrogen bonds between the guanidinium group of arginine and a nucleic acid base of Poly-IC may allow the formation of highly immunogenic molecular conplexes.

The arginine-containing peptides can associate with Poly-IC via either one (or both) of these interactions: 1) The strong positive charge of the arginine guanidinium group (—NH—$CNH_2$—$NH_2^+$) and negative charges of the PO— groups of the polynucleotide chains serve as strong electrostatic (aka, salt bridge) interactions (FIG. 4); 2) Hydrogen (H)-bonds between the guanidinium and the nucleotide bases (FIG. 5). Although Poly-IC is double stranded, most preparations are quite heterogeneous (poly-I and poly-C of various sizes) thus there are many unpaired bases capable of forming H-bonds with arginine.

As mentioned above, the use of another natural cationic amino acid, lysine (K) has not resulted in enhanced immunogenicity, suggesting that either H-bonds are more important (K cannot make H-bonds with nucleic acids) or that the strength and nature of the electrostatic interaction between K and Poly-IC differs substantially (either stronger or weaker) from the one between R and Poly-IC.

In some instances, lysine residues may be successfully added to the peptide to enhance immunogenicity. Peptides with K tails could form complexes with poly-IC via electrostatic interactions but may not undergo the necessary antigen processing (peptide trimming or transport to the endoplasmic reticulum) to form the peptide-MHC complexes recognized by T cells. Lysine tails having a length of less than 7 amino acids added to the epitope may allow the peptide to fold in the specific conformation needed to enhance interaction with Poly-IC. Between about 1 to about 10 lysine residues may be added to a peptide, preferably at the amino terminus, however the residues may in some cases be added to the carboxy terminus.

Example 2—Addition of Hydrophobic Residues

Figure 6:
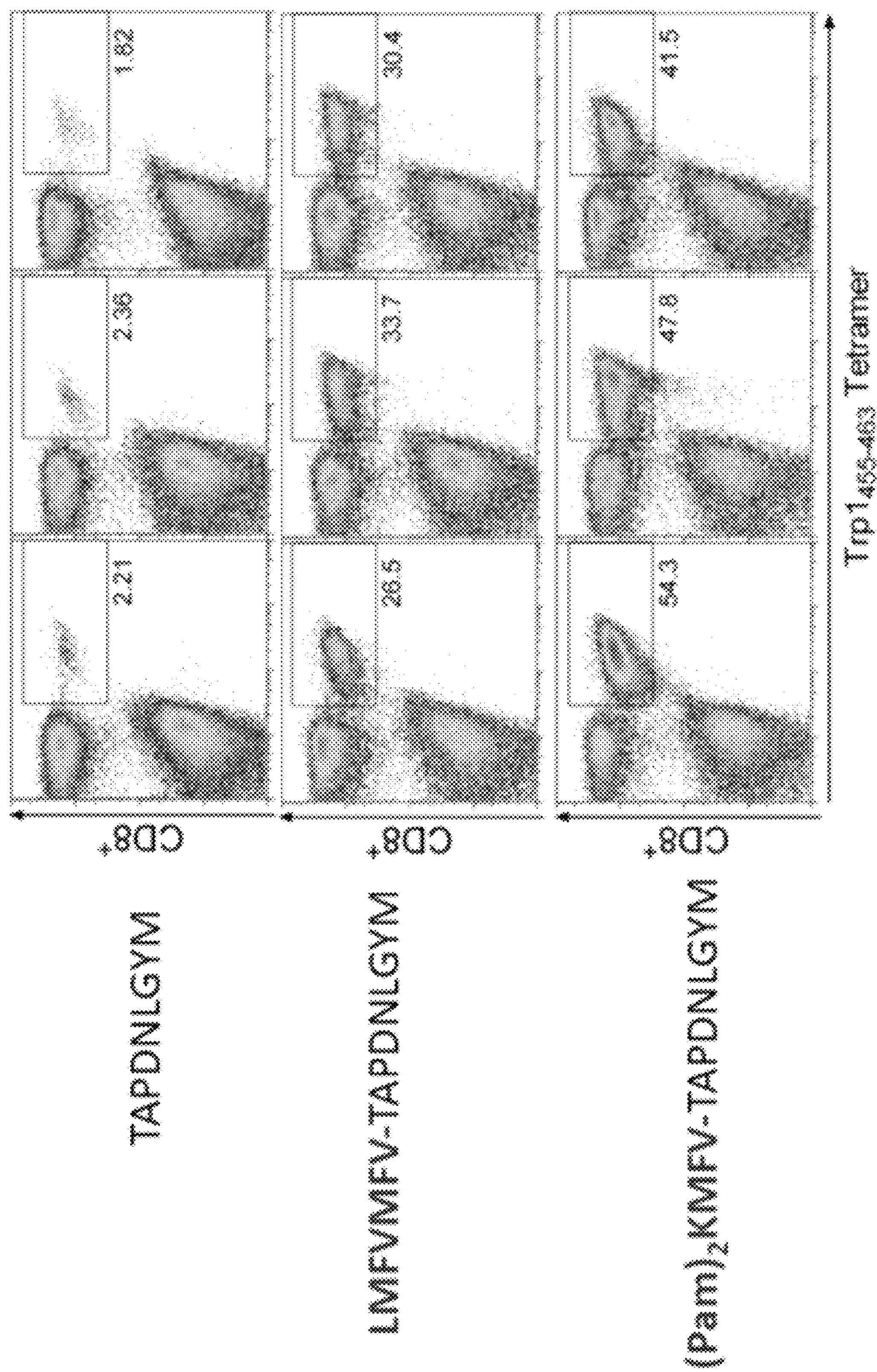
FIG. 6 is an image depicting the hydrophobic tails increase the immunogenicity of a peptide epitope. CD8 T cell responses of peptide epitope $Trp1_{455/9M}$ (TAPDNLGYM) (SEQ ID NO:2) containing 2 types of hydrophobic tails (LMFVMFV-TAPDNLGYM (SEQ ID NO:10) and $(Pam)_2$KMFV-TAPDNLGYM (SEQ ID NO:11)) at the amino terminus end were measured by tetramer analysis after i.v. prime-boost (2 weeks apart) vaccination using peptide mixed with 50 μg Poly-IC. Immune responses in 3 individual mice measured 7 days after the boost in blood samples. Numbers below the rectangular gates correspond to the % tetramer positive (antigen-specific) cells of the total CD8 T cell population.

Increasing the hydrophobicity of the peptide epitopes, for example by the addition of a 7 hydrophobic amino acid chain or fatty acid chains (linked to the peptide via 3 hydrophobic residues), also results in a dramatic increase in the immunogenicity of the peptide epitopes (FIG. 6). Some hydrophobic residues with aromatic rings such as phenylalanine (F) and tryptophan (W) may form stacking interactions with the nucleotide bases, resulting in the formation of peptide-nucleic acid complexes. Similarly, small (between about 3 to about 12 amino acids) linear hydrophobic amino acid sequences (LMFMFV) (SEQ ID NO:12) or lipids (e.g., palmitic acid, or Pam) attached to the peptide form interactions with hydrophobic regions of the nucleic acids (e.g., intercalating themselves between base pairs). Between about 3 and about 20 hydrophobic amino acids may be added to the peptide to enhance immunogenicity. Preferably, the hydrophobic amino acids are added at the N terminus, however the amino acids may also be added at the C terminus. If the epitope itself is hydrophobic (such as SVDFFVWL (SEQ ID NO:13)), it may only require 3 hydrophobic amino acids to enhance immunogenicity, such as the addition of MVF. Alternatively, if the epitope itself is hydrophilic, (such as in TAPDNLGYM (SEQ ID NO:2)), it may require the addition of at least 6 hydrophobic amino acid residues, such as the addition of MFVMFV (SEQ ID NO:1). Any lipid may be used in the present invention as lipids increase hydrophobicity.

Figure 7:
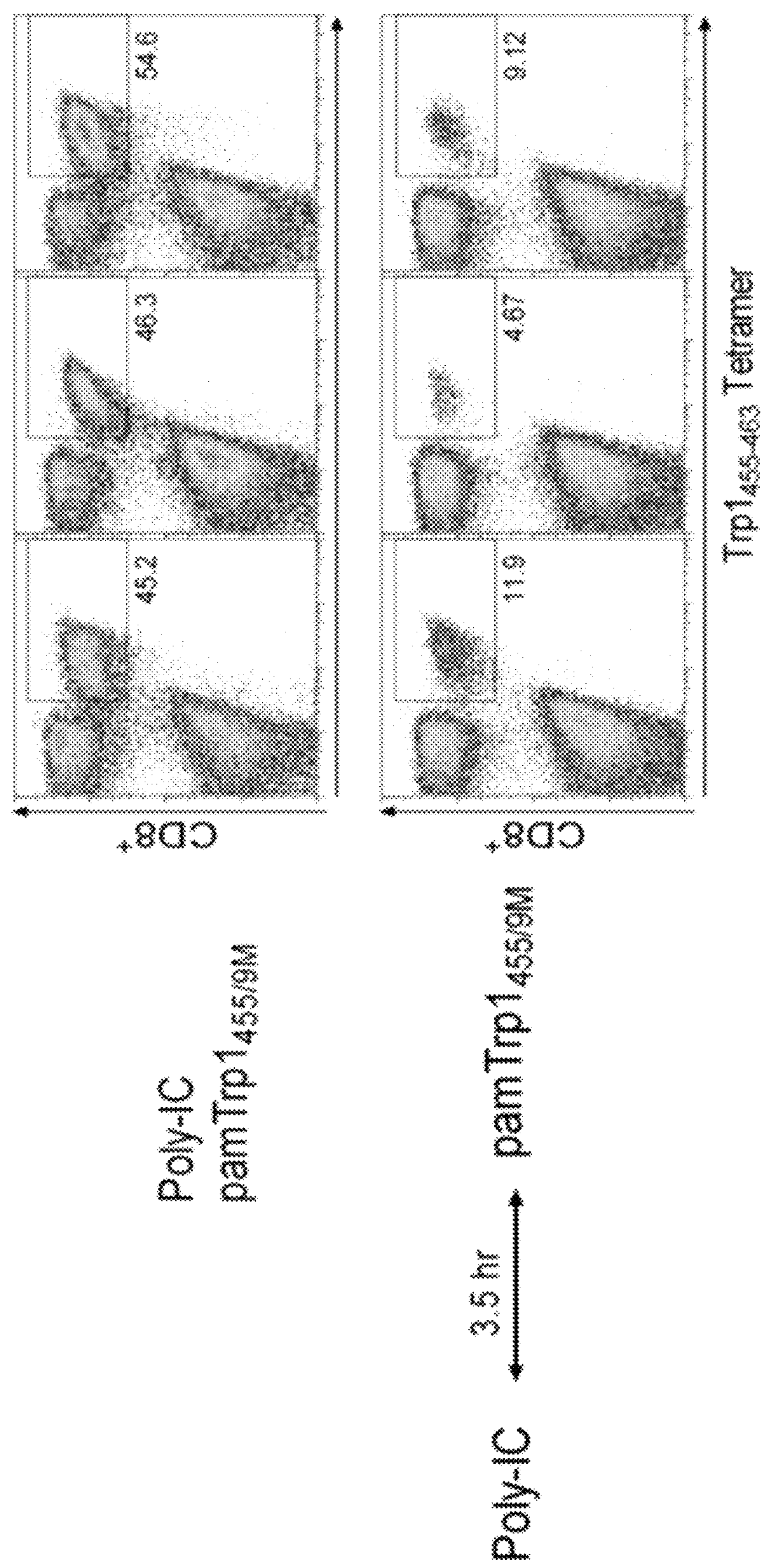
FIG. 7 is an image depicting that the simultaneous administration of peptide and Poly-IC generates stronger immune responses as compared to injections 3.5 hours apart. Comparison of CD8 T cell responses of peptide epitope $(pam)_2$ $Trp_{455/9M}$ [$(Pam)_2$KMFV-TAPDNLGYM] (SEQ ID NO:11) injected together with 50 μg Poly-IC (top panels) or 3.5 hours after the Poly-IC (bottom panels). Immune response in 3 individual mice measured 7 days after an identical boost (12 days apart) in blood samples. Numbers below the rectangular gates correspond to the % tetramer positive (antigen-specific) cells of the total CD8 T cell population.

Arginine-containing peptides and the hydrophobic peptides are highly immunogenic when administered together with Poly-IC because they are able to form complexes. This is supported by the observations that if the Poly-IC is injected intravenously (i.v) 3.5 to 5 hr before the peptide (also i.v.), then the immune responses are dramatically lower as compared to circumstances when both peptide and Poly-IC are administered together (FIGS. 7 and 8). Poly-IC administered before the peptide is rapidly captured via scavenger receptors by the antigen-presenting cells and by the time the peptide is injected hours later, few complexes can be formed in vivo and the peptide is less effective in specifically reaching the antigen-presenting cells.

While Poly-IC has been used in the preceding examples, other immune adjuvants may be used such as synthetic oligodeoxynucleotides (ODNs) with a CpG motif as well as modified polyinosinic:polycytidylic acid (Poly-IC). Non-limiting examples of modified Poly-ICs include, but are not limited to, Poly-IC/LC (Hiltonol) and Poly-IC12U (Ampligen).

Figure 9:
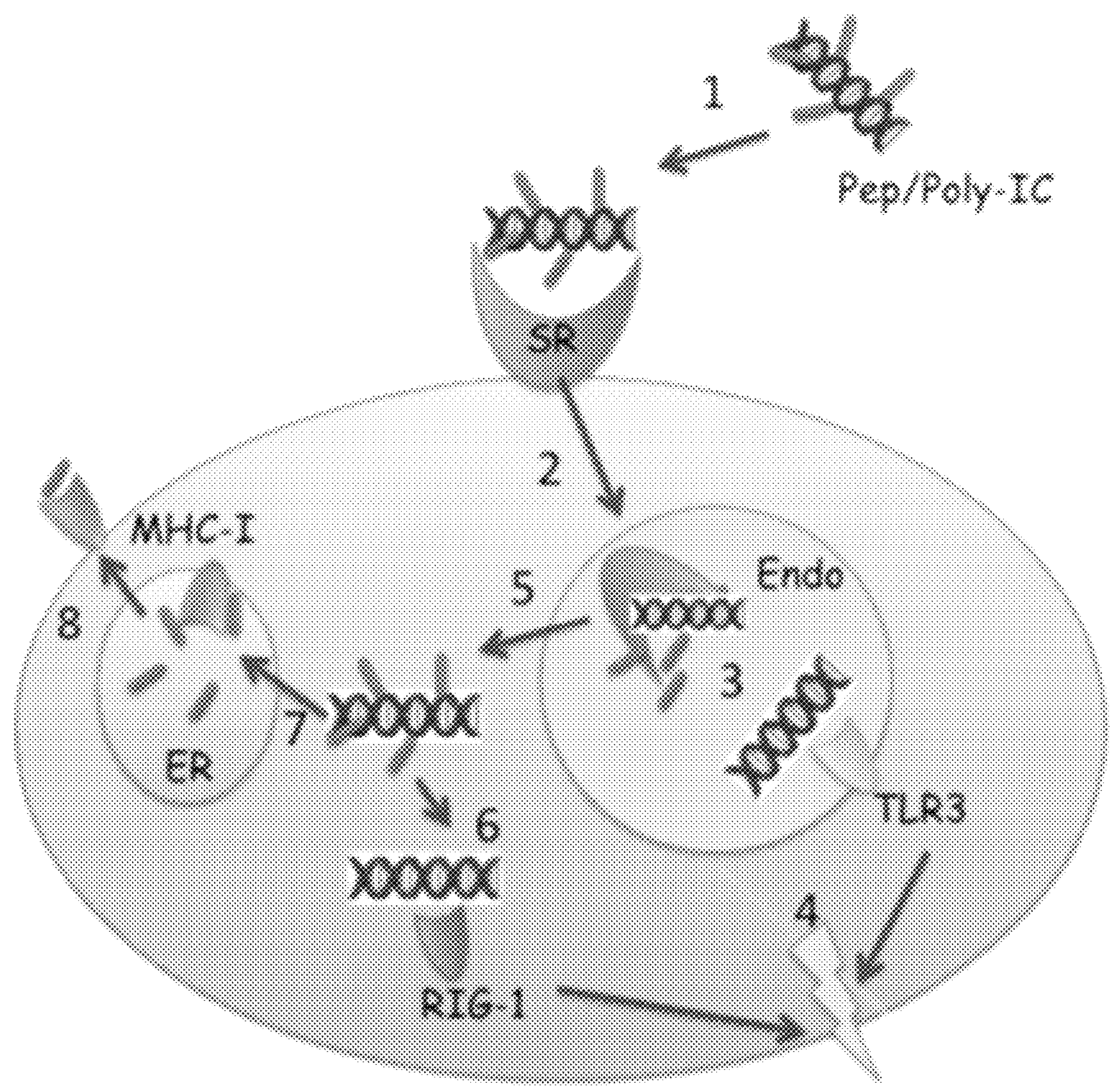
FIG. 9 is an image depicting the high immunogenicity of peptide/Poly-IC complexes. 1: Peptide/Poly-IC complex binds to scavenger receptor (SR) on antigen presenting cell (APC). 2: The complex is internalized to endosomes (Endo). 3: Poly-IC binds to TLR3. 4: Stimulated TLR3 activates the APC. 5: Pep/Poly-IC complexes can escape to cytosol. 6: Poly-IC can stimulate RIG-1 helicases and further activate the APC (4). 7: Peptides in the cytosol are transported to the endoplasmic reticulum (ER), where they can be processed and trimmed (if necessary) and bind to empty MHC-I molecules. 8: Peptide/MHC-I complexes are transported to the cell surface where they can be presented to the antigen receptor of T-cells.

The inventors have built a model to explain why the peptide/Poly-IC complexes exhibit high immunogenicity (FIG. 9). This model proposes that these complexes can be efficiently captured by antigen-presenting cells that become highly activated via TLR3 and/or cytoplamic helicase (RIG-I-like receptors) stimulation and are then able to present the immunogenic peptide to the antigen-specific T cells. 1: Peptide/Poly-IC complex binds to scavenger receptor (SR) on antigen presenting cell (APC). 2: The complex is internalized to endosomes (Endo). 3: Poly-IC binds to TLR3. 4: Stimulated TLR3 activates the APC. 5: Pep/Poly-IC complexes can escape to cytosol. 6: Poly-IC can stimulate RIG-1 helicases and further activate the APC (4). 7: Peptides in the cytosol are transported to the endoplasmic reticulum (ER), where they can be processed and trimmed (if necessary) and bind to empty MHC-I molecules. 8: Peptide/MHC-I complexes are transported to the cell surface where they can be presented to the antigen receptor of T-cells.

The inventors are developing assays that measure the formation of these complexes. The data has been observed with Poly-IC, which is both a TLR3 agonist and ligand for RIG-1 like receptors, or cytoplasmic helicases. However, it is believed that the adjuvant effects occur through RIG-1 like receptors, and not TLR3 because poly-AU (specific TLR3 agonist) cannot enhance the immunogenicity of the modified peptides (data not shown). In addition, a TLR9 agonist (CpG) does not enhance the immunogenicity.

The data indicates that increased peptide immunogenicity is conferred by N-terminal arginine (R) residues and not lysines (K), which are also positively charged. The inventors also assess whether C-terminal R's confer enhanced immunogenicity. The inventors have presented examples of 2 different peptide epitopes having an R at the amino terminus end resulting in increased immunogenicity. These observations can be extended to additional epitopes, including epitopes that would be used in humans (e.g., using HLA-A2 transgenic mice).

Covalent Bonds for Conjugating Peptides to Immune Adjuvant

While hydrogen bonds and electrostatic interactions are important, the inventors have reasoned that conjugating peptides corresponding to T cell epitopes to poly-K via covalent bonds will ensure that the peptides are now tightly bound to the poly-ICLC adjuvant thus removing any uncertainty as to whether or not a peptide spontaneously binds to the adjuvant. Covalent bonds may be made from the peptide to any immune adjuvant or its components including, but not limited to, Poly-K, Poly-IC and carboxymethyl cellulose (CMC). The peptides are linked to the immune adjuvant through additional residues at either the N end or the C end of the peptide. The additional residues can be linked with or without the use of spacers such as C-SS. Spacers comprised of hydrophilic residues may be used to increase the solubility of epitopes that are hydrophobic thus making it easier to carry out the chemical reactions.

In the example used herein, poly-K is used. Because poly-K contains a multitude of amino (—NH2) groups (each lysine in the polymer has an —NH2 group in its side chain), it becomes feasible to utilize a chemical cross-linking reagent (CLR) to covalently bind multiple synthetic peptide molecules to a single poly-K molecule. Numerous CLRs exist and have been used to conjugate small molecules such as peptides to carriers (proteins or poly-K) to produce antibodies. Any type of CLR can be used depending on the characteristics of the immune adjuvant as well as the characteristics of the modified peptide that is to be joined to the immune adjuvant. The synthetic peptide can be linked to the amino groups of poly-K via carboxyl (—COOH) groups of aspartic acid (D) glutamic acid (E) or the terminus carboxyl group of the peptide. Other CLRs can be used to join the peptide to poly-K using amino groups of the peptide contained in lysine (K), arginines (R), or the amino-terminus group of the peptide.

Another type of CLR such as succinimidyl-4-(N-maleimidomethyl)cyclohexane-1-carboxylate (SMCC) can be used to link the peptide containing a cysteine (C), which has a sulfhydryl (—SH) group to the poly-K. The use of SMCC to conjugate peptides to poly-K is ideal because it will avoid modifying —NH2 and —COOH in the peptide contained by frequently found amino acids such as K, R, D and E, which could modify in a deleterious manner, the immunogenicity of T cell epitope.

On the other hand, the occurrence of C residues in protein antigens and T cell peptide epitopes is more rare and in the event that they are found, these can be substituted with other residues (e.g., serine or alpha-amino butyric acid) not containing —SH groups. Thus, a C residue can be added to either side of a known T cell epitope to facilitate the conjugation of a peptide to poly-K.

In the example below, the inventors demonstrate the conjugation of a T cell epitope from tyrosinase-related protein 1 (Trp1), which is recognized by melanoma-reactive CD8 T cells in mice, to poly-K using SMCC as the CLR. A C residue was added with a hydrophilic amino acid linker (SS) (SEQ ID NO:14) to the minimal T cell epitope, TAPDNLGYM (SEQ ID NO:2). The resulting peptide, CSSTAPDNLGYM (SEQ ID NO:15) was conjugated to poly-K and the complex was formulated with CMC and poly-IC to prepare the vaccine.

Example 3—Preparation of a Trp1 Peptide/Poly-ICLC Complex Vaccine

Synthetic peptide epitopes are linked to poly-L-lysine (poly-K) using a bi-functional protein conjugation agent (SMCC) via a —SH on the peptide and —NH2 groups on poly-K. The unconjugated peptide and SMCC are eliminated using desalting columns or dialysis. The peptide/poly-K conjugate is then adsorbed onto carboxymethyl cellulose (CMC) prior to incorporating the poly-IC to prevent aggregation.

Thirty-two vaccine injections were prepared using 50 ug poly-IC and 200 ug peptide per injection.

Materials and Methods 2.5 mg poly-K (Sigma, 25,000 Da MW; normally for 1 mg of poly-IC, 0.75 mg of poly-K is used, here the inventors used ~2×)=16.6×10E−6 moles of K; 50 ug×32=1.6 mg Poly-IC (Sigma); 200 ug×32=6.4 mg Cys-containing peptide (CSSTAPDNLGYM) (SEQ ID NO:8)=5×10E−6 moles; 4 mg CMC-Hi density (for 1 mg poly-IC, 2.5 mg CMC are used=0.2 ml @20 mg/ml); 2 mg No-Weigh Sulfo-SMCC (Thermo Scientific) dissolved in 0.2 ml ddH2O (10 mg/ml)= 4.6 ×10−6 moles; sterile PBS; sterile normal saline; and a small Zeba-Spin desalting column (Thermo).

To prepare the vaccine injections, first the poly-K was prepared at 10 mg/ml by dissolving 2.5 mg powder in 0.25 ml PBS. The peptide was dissolved at 10 mg/ml in dH20. The peptide may be warmed if necessary to dissolve completely.

0.2 ml sulfo-SMCC (~4:1 molar ratio) was added to the 0.25 ml poly-K in PBS (0.45 ml total) and incubated at RT for 30 minutes.

50 ul PBS was added to the mixture (0.5 ml total). The mixture was desalted in a Zeba-Spin Column pre-equilibrated with PBS.

The sample (~0.5 ml) was collected and 0.640 ml peptide (6.4 mg) was added to the 0.5 ml activated poly-K for a final volume of ~1.1 ml. The sample was incubated for 30-45 minutes and subsequently desalted in a Zeba-Spin Column pre-equilibrated with saline.

If the solution was clear, filter-sterilization was performed. 1.0 ml will be needed for next step.

In a hood with sterile materials, 100 ul of poly-K/peptide was added to 0.2 ml of sterile CMC, (20 mg/ml). The solution was mixed well and was allowed to continue mixing for about 10 minutes. This last step may be repeated 9 additional times until all the poly-K/peptide is used. Once all the poly-K/peptide is used, the solution may be left mixing for about 24 hours for a final volume of ~1.2 ml.

After 24 hours, the solution may be checked for turbidity and allowed to mix about 1-3 additional days if necessary.

Poly-IC is then prepared at 4 mg/ml in sterile saline. (e.g. 2 mg into 0.5 ml). 0.4 ml of poly-IC is added in 50 ul aliquots (8 additions) every 30 minutes while continuously mixing.

Turbidity is checked and the solution may be mixed about 1-3 additional days if necessary. The final volume should be 1.6 ml.

1.6 ml saline is added to the above solution for a final volume of about 3.2 ml. The amount of peptide incorporated into the complex is measured using a BCA protein kit. Results indicate that 50% of the peptide was incorporated into the complexes.

The solution is stored by refrigeration, not frozen and 100-200 ul is used per injection (50-100 ug of peptide).

Immunogenicity Evaluation

Figure 10A:
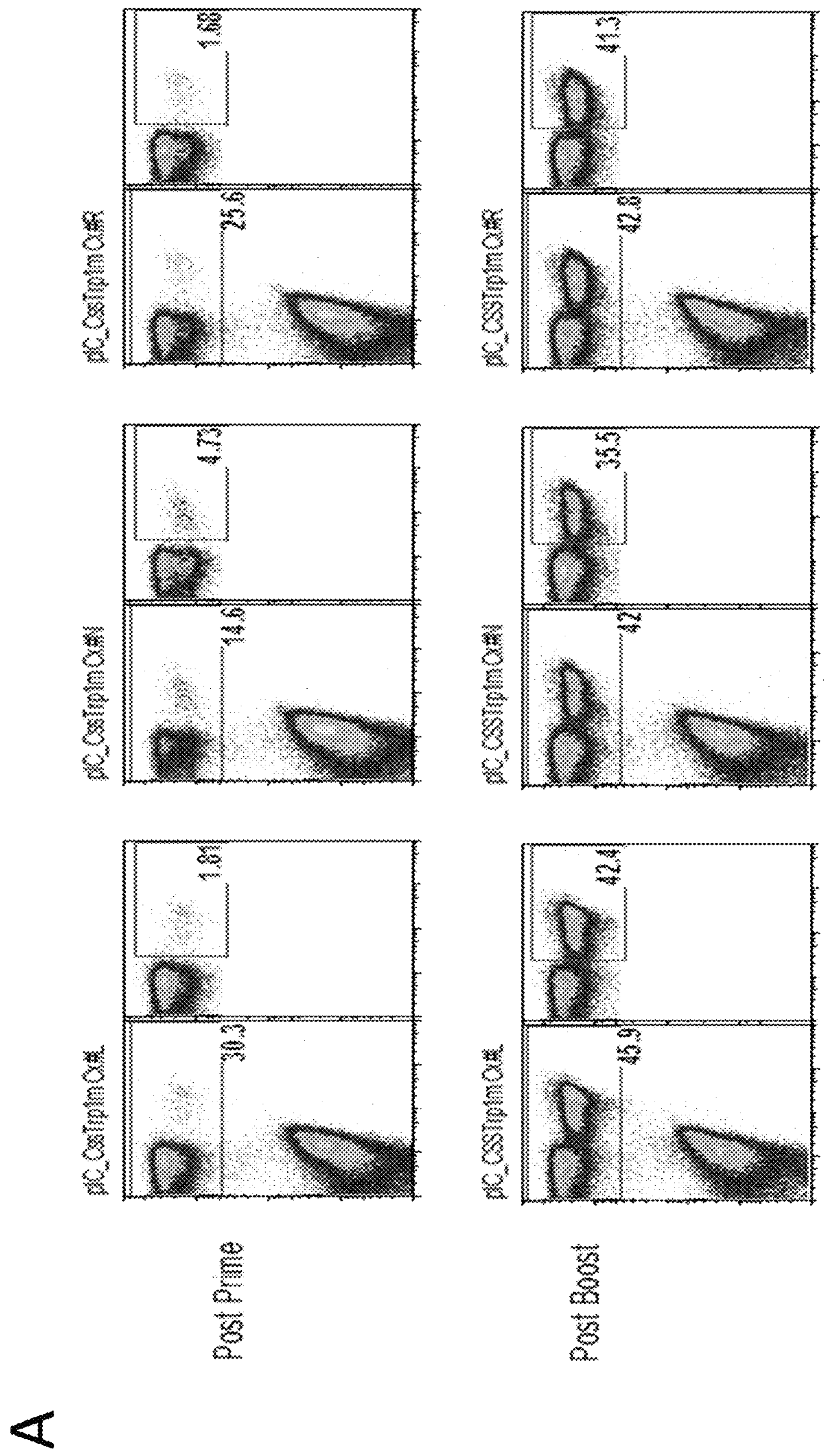
FIG. 10A is a series of images illustrating the peptide/poly-ICLC complex vaccine elicits potent immune responses. Mice (3/group) were immunized with a peptide/poly-ICLC conjugate vaccine (panel A). Immune responses were measured by tetramer analysis 6 days after the prime and boost immunizations as noted. Numbers on each rectangular gate represent the % of cells within the gate. The plots on the right side of each of the 12 determinations calculate the % of tetramer positive CD8 T cells (antigen-specific) in each determination. The plots on the left side calculate the % CD8 T cells (total). Specifically, the 3 mice vaccinated with the peptide/poly-ICLC conjugate had 42.4, 35.5 and 41.3% tetramer positive CD8 T cells after the boost.
Figure 10B:
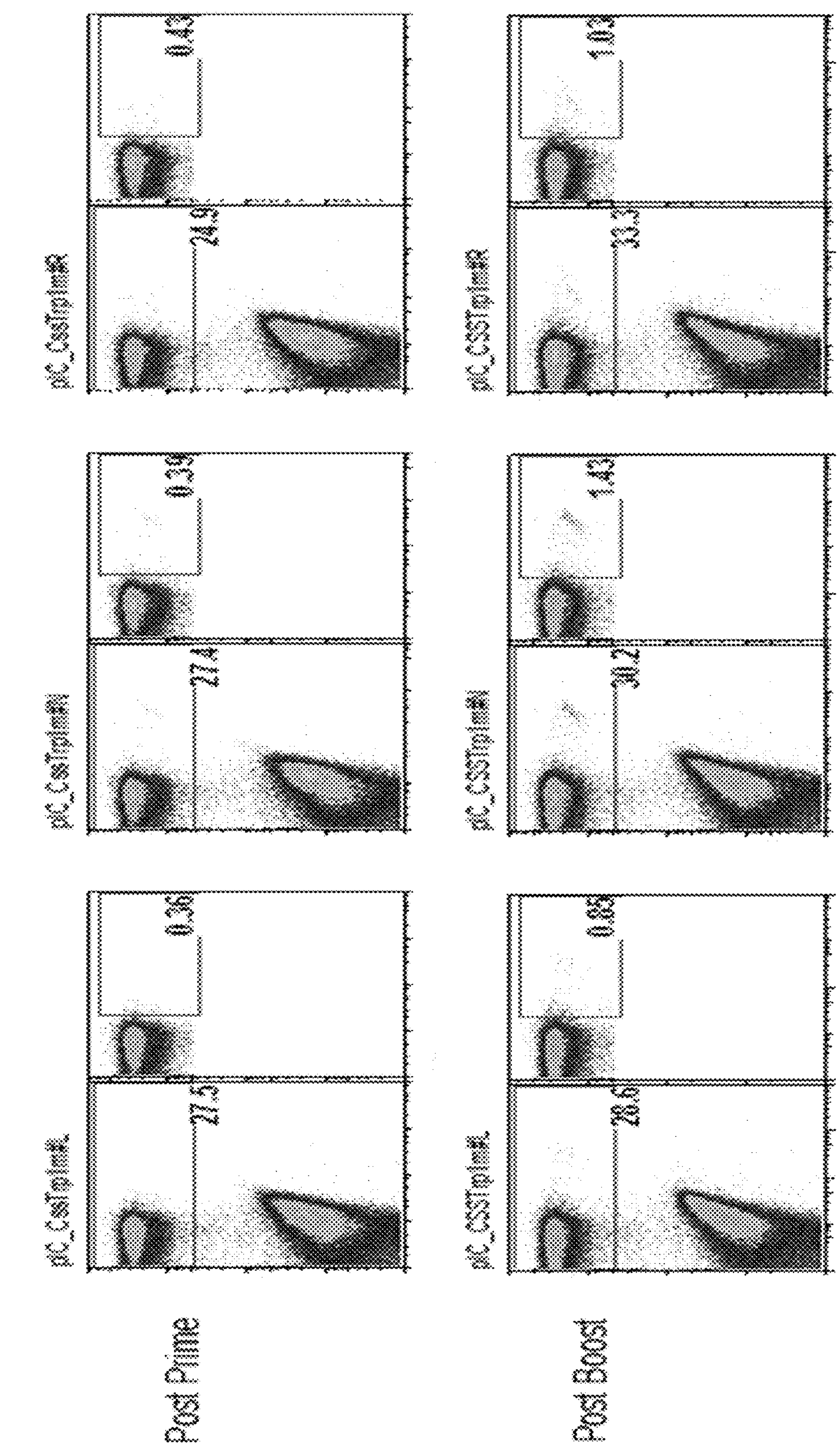
FIG. 10B is a series of images illustrating the peptide/poly-ICLC complex vaccine elicits potent immune responses. Mice (3/group) were immunized with a vaccine prepared with the same amounts of peptide and poly-IC, mixed but not conjugated (panel B). Immune responses were measured by tetramer analysis 6 days after the prime and boost immunizations as noted. Numbers on each rectangular gate represent the % of cells within the gate. The plots on the right side of each of the 12 determinations calculate the % of tetramer positive CD8 T cells (antigen-specific) in each determination. The plots on the left side calculate the % CD8 T cells (total). Specifically, the 3 mice that received the control vaccine had 0.85, 1.43 and 1.03% tetramer positive CD8 T cells.

Mice (3 per group) were immunized intravenously with 200 ul of peptide/poly-ICLC complex vaccine or a control vaccine prepared by simply mixing the CSSTAPDNLGYM (SEQ ID NO:15) peptide with poly-IC (using the same amounts found in the complex). All mice received 2 sequential immunizations (Prime/boost) 12 days apart and immune responses were measured by tetramer analyses in blood samples six days after each immunization. After the prime, the mice immunized with the peptide/poly-ICLC complex vaccine had an average of 2.7% tetramer positive CD8 T cells in blood, while the mice vaccinated with the control (unconjugated) peptide vaccine had 0.4% tetramer positive cells (6.8-fold difference). After the second immunization the differences in immune responses were more dramatic. The mice immunized with the peptide/poly-ICLC complex vaccine had an average of 39.7% tetramer positive CD8 T cells in blood, and the mice vaccinated with the control (unconjugated) peptide vaccine had 1.1% tetramer positive cells (36.1-fold difference). The raw data (dot plot analyses) of these results is shown in FIG. 10.

There are examples of antigens (proteins or peptides) that are conjugated to antibodies specific for cell surface molecules expressed on antigen-presenting cells in order to specifically target the antigens to these cells to generate immune responses. There are also examples of conjugating peptides to small synthetic oligodeoxynucleotides (ODN) containing CpG motifs (ODN-CpG) in order to increase the immunogenicity of the peptides. Both of these approaches slightly increase the immunogenicity but not to the extent that the inventors have observed with the peptide-poly-IC complexes. This is likely due to the antibodies, while targeting the antigen to the appropriate antigen-presenting cell, are not sufficiently stimulatory to activate the cell to become optimal to stimulate the T cell responses. In addition, the ODN-CpG-peptide complexes are not captured as efficiently due to their relatively small size, as compared to the peptide-poly-IC complexes, by the scavenger receptors on the antigen-presenting cells. In addition, the inventors have shown that CpG-ODN adjuvant is quite inefficient to generate secondary (booster) immune responses, while poly-IC is very potent in achieving the secondary T cell responses, which are critical for generating the huge numbers of antigen-specific T cells that are observed with the peptide-poly-IC complexes. The methods for manufacturing antibody-antigen complexes and ODN-CPG-peptide conjugates are significantly more complicated as compared to the preparation of the peptide-poly-IC complexes.

The approach detailed herein conjugates the peptide indirectly to the adjuvant or the targeting molecules, which in both instances is poly-IC. In the example presented herein, the peptide is conjugated to the poly-K polymer, which associates with the poly-IC via numerous non-covalent charge bonds (anionic phosphate groups of poly-IC with cationic amino groups of poly-K). The CMC in this formulation prevents the formation of insoluble large aggregates that would impede drug formulation and use in patients.

The conjugation of peptide to the poly-IC/poly-K complex ensures simultaneous arrival of the poly-IC and antigen to the antigen-presenting cells. The data show that poly-IC administered about 3-5 hours prior to the injection of the peptide results in poor immune responses. Furthermore, injection of poly-IC or Poly-I (which binds to scavenger receptors but does not function as immune adjuvant) prior to the injection of peptide-poly-IC complexes results in inhibition of the immune responses, possibly by competing with scavenger receptors and decreasing the amount of antigen captured by antigen-presenting cells.

The inventors have presented an example of a procedure on how to prepare a highly immunogenic peptide-based vaccine to induce very large T cell responses. This procedure involves the conjugation of a synthetic peptide containing a C residue to poly-K using a bi-functional cross-linking reagent (SMCC). The peptide/poly-K complex was then formulated with CMC and poly-IC to produce a self-adjuvant vaccine that was 36-fold more effective as compared to the same peptide administered mixed with the same adjuvant (but not complexed to it). The results presented here should apply to any peptide representing a T cell epitope for anti-tumor or anti-infectious agent therapies.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of eliciting an antigen-specific T cell response in a subject comprising:

obtaining a vaccine comprising:

an immune adjuvant wherein the immune adjuvant is a synthetic nucleic acid inducing a cell-mediated response and selected from the group consisting of polyinosinic:polycytidylic acid (Poly-IC), Poly-IC/LC, Poly-K, Poly-IC12U, and carboxymethyl cellulose (CMC); and a modified peptide comprising:

a T cell epitope for infectious agents or tumor antigens wherein the T cell epitope is between 8 to 15 amino acids in length;

a short hydrophobic amino acid linker; and at least one arginine (R) residue wherein the at least one arginine residue is appended to an amino or a carboxy terminal end of the T-cell epitope;

wherein the modified peptide consists of the T-cell epitope, the short hydrophobic amino acid linker, and the at least one arginine residue without any additional amino acids;

wherein interaction of the immune adjuvant and the modified peptide form a complex; and administering the vaccine to the subject wherein the vaccine elicits an antigen-specific T cell response in the subject.

2. The method of claim 1, wherein the at least one arginine residue is added to the amino terminal end of the T-cell epitope.

3. The method of claim 1, wherein between about 3 to about 10 of the arginine residues are added to the T-cell epitope.

4. The method of claim 1, wherein the immune adjuvant is complexed to the modified peptide via covalent bonds.

5. The method of claim 1, wherein a chemical cross-linking reagent is used to complex the immune adjuvant to the at least one modified peptide.

6. A method of eliciting an antigen-specific T cell response in a subject comprising:
- obtaining a vaccine comprising:
  - an immune adjuvant wherein the immune adjuvant is selected from the group consisting of polyinosinic: polycytidylic acid (Poly-IC), Poly-IC/LC, Poly-K, Poly-IC12U, and carboxymethyl cellulose (CMC); and
  - a modified peptide comprising:
    - a known T cell epitope for infectious agents or tumor antigens wherein the T cell epitope is between 8 to 15 amino acids in length; and
    - between about 3 to about 20 hydrophobic residues wherein the hydrophobic residues are appended to an amino or a carboxy end of the T-cell epitope;
    - wherein the hydrophobic residues are selected from the group consisting of hydrophobic residues having aromatic rings, small linear hydrophobic amino acid sequences having at least 6 amino acid residues, and lipids;
  - wherein interaction of the immune adjuvant and the modified peptide form a complex; and
- administering the vaccine to the subject wherein the vaccine elicits an antigen-specific T cell response in the subject.

7. The method of claim 6, wherein the hydrophobic residues are aromatic rings selected from the group consisting of phenylalanine (F) and tryptophan (W).

8. The method of claim 6, wherein the hydrophobic residues are added to the amino terminal end of the T-cell epitope.

9. The method of claim 6, further comprising the modified peptide being further modified by the addition of at least 1 arginine (R) residue.

10. A method of eliciting an antigen-specific T cell response in a subject comprising:
- obtaining a vaccine comprising:
  - an immune adjuvant wherein the immune adjuvant is selected from the group consisting of polyinosinic: polycytidylic acid (Poly-IC), Poly-IC/LC, and Poly-IC12U; and
  - a modified peptide comprising:
    - a known T cell epitope for infectious agents or tumor antigens wherein the T cell epitope is between 8 to 15 amino acids in length;
    - at least one hydrophilic amino acid linker; and
    - a cysteine (C) residue wherein the cysteine residue is appended to an amino or a carboxy end of the T-cell epitope;
    - wherein the modified peptide consists of the T-cell epitope, the at least one hydrophilic amino acid linker and the cysteine residue without any additional amino acids;
  - wherein the modified peptide is conjugated via covalent bonds to a polymer selected from the group consisting of Poly-K, Poly-IC and carboxymethyl cellulose (CMC) using a chemical cross-linking reagent (CLR) to form a conjugate;
  - wherein interaction of the immune adjuvant and the conjugate form a complex; and
- administering the vaccine to the subject wherein the vaccine elicits an antigen-specific T cell response in the subject.

11. The method of claim 10, wherein a chemical cross-linking reagent (CLR) is used to complex the immune adjuvant to the at least one modified peptide.

12. The method of claim 11, wherein the CLR is succinimidyl-4-(N-maleimidomethyl)cyclohexane-1-carboxylate (SMCC).

13. The method of claim 10, wherein the cysteine residue is added to the amino terminal end of the T-cell epitope.

* * * * *